(12) United States Patent
Cote et al.

(10) Patent No.: US 8,757,378 B2
(45) Date of Patent: Jun. 24, 2014

(54) PACKAGING FOR SURGICAL BLADE TIPS

(75) Inventors: Dana Cote, Boxford, MA (US); Robert DeMarinis, North Attleboro, MA (US); Gregory P. Halloran, Grafton, MA (US); Thomas F. Walsh, Stoneham, MA (US); Jessica Chiappone, Boston, MA (US)

(73) Assignee: Beaver-Visitec International (US), Inc., Lake Forest, IL (US)

( * ) Notice: Subject to any disclaimer, the term of this patent is extended or adjusted under 35 U.S.C. 154(b) by 194 days.

(21) Appl. No.: 12/750,928

(22) Filed: Mar. 31, 2010

(65) Prior Publication Data

US 2010/0252467 A1    Oct. 7, 2010

Related U.S. Application Data

(60) Provisional application No. 61/166,462, filed on Apr. 3, 2009.

(51) Int. Cl.
*A61B 17/3215*    (2006.01)
*B26B 1/00*    (2006.01)

(52) U.S. Cl.
USPC .............. 206/363; 206/349; 206/355; 30/329

(58) Field of Classification Search
USPC ................ 206/363, 349, 352, 355, 359, 353; 301/329, 330, 337, 340; 30/329, 330, 30/337, 340
See application file for complete search history.

(56) References Cited

U.S. PATENT DOCUMENTS

| 3,793,726 | A |   | 2/1974  | Schrank                     |
| 4,576,164 | A | * | 3/1986  | Richeson ............ 606/167 |
| 4,927,018 | A | * | 5/1990  | Yang et al. ......... 206/365 |
| 4,985,034 | A |   | 1/1991  | Lipton                      |
| 5,059,210 | A | * | 10/1991 | Clark et al. ........ 606/169 |
| 5,105,823 | A | * | 4/1992  | Blum ................ 600/567 |

(Continued)

FOREIGN PATENT DOCUMENTS

| DE | 3724912 A1    | 2/1988 |
| EP | 0 988 832 A2  | 3/2000 |
| GB | 2 411 857 A   | 9/2005 |
| JP | 2007228989    | 9/2007 |

*Primary Examiner* — Anthony Stashick
*Assistant Examiner* — Ernesto Grano
(74) *Attorney, Agent, or Firm* — Hoffmann & Baron, LLP (57) ABSTRACT

A package for a surgical blade tip is provided herein. The package cooperates with the surgical blade tip to properly retain it and facilitate mounting onto a surgical blade handle. In one aspect, the invention includes a package having a body with a side wall and at least two detents extending inwardly from the side wall. In addition, a surgical blade tip is provided having an adaptor with a blade extending therefrom. The adaptor includes at least two recesses formed therein. The surgical blade tip is disposed in the package with the detents being at least partially inserted into the recesses. Also, the detents are configured to apply a retentive force to the adaptor to retain the adaptor in a first position and configured to deflect with a predetermined amount of torque being applied to the surgical blade tip so as to permit the adaptor to rotate from the first position to a second position where the detents are not inserted into the recesses. Advantageously, with the subject invention, a package may be provided which maintains a blade of a surgical blade tip in spaced relationship so as to minimize contamination thereof. In addition, the interengagement of the detents and the recesses allows for proper retention of the surgical blade tip during mounting onto a surgical blade handle.

17 Claims, 10 Drawing Sheets

(56) References Cited

U.S. PATENT DOCUMENTS

| | | | | |
|---|---|---|---|---|
| 5,342,380 A | * | 8/1994 | Hood | 606/169 |
| 5,498,244 A | * | 3/1996 | Eck | 604/198 |
| 5,695,510 A | * | 12/1997 | Hood | 606/169 |
| 5,830,226 A | * | 11/1998 | Webb et al. | 606/167 |
| 6,960,200 B2 | * | 11/2005 | Shapeton et al. | 606/1 |
| 2007/0255298 A1 | | 11/2007 | Djordjevic et al. | |
| 2008/0196253 A1 | * | 8/2008 | Ezra et al. | 30/124 |
| 2008/0230423 A1 | | 9/2008 | Loeffler et al. | |

\* cited by examiner

PACKAGING FOR SURGICAL BLADE TIPS

FIELD OF THE INVENTION

This invention relates to packaging for surgical blade tips.

DESCRIPTION OF THE PRIOR ART

Packaging for surgical blade tips is known in the prior art. In the prior art, surgical blade tips are typically offered in two forms, those that require collets for assembly to surgical blade handles and those that are in plastic tips that do not require collets for assembly to the surgical blade handles. Both forms of blade tips are assembled by hand or the use of a mechanical device such as a hemostat. This is a typically unsafe operation due to an exposed point or cutting edge. Surgical blade handles are typically provided with a collet which is used re-usably with single-use packaged surgical blade tips. The blade handle is sterilized between uses, including the collet. Due to the structure of the collet, sterilization may be difficult. In addition, the collet is often misplaced or lost and must be replaced for use. In the prior art, surgical blades with plastic tips are typically assembled to the surgical blade handles.

SUMMARY OF THE INVENTION

A package for a surgical blade tip is provided herein. The package cooperates with the surgical blade tip to properly retain it and facilitate mounting onto a surgical blade handle. In one aspect, the invention includes a package having a body with a side wall and at least two detents extending inwardly from the side wall. In addition, a surgical blade tip is provided having an adaptor with a blade extending therefrom. The adaptor includes at least two recesses formed therein. The surgical blade tip is disposed in the package with the detents being at least partially inserted into the recesses. Also, the detents are configured to apply a retentive force to the adaptor to retain the adaptor in a first position and configured to deflect with a predetermined amount of torque being applied to the surgical blade tip so as to permit the adaptor to rotate relative to the body from the first position to a second position where the detents are not inserted into the recesses. Advantageously, with the subject invention, a package may be provided which maintains a blade of a surgical blade tip in spaced relationship so as to minimize contamination thereof. In addition, the interengagement of the detents and the recesses allows for proper retention of the surgical blade tip during mounting onto a surgical blade handle.

These and other features of the invention will be better understood through a study of the following detailed description and accompanying drawings.

DETAILED DESCRIPTION OF THE INVENTION

With reference to the Figures, a combination 10 is shown of a package 12 with a surgical blade tip 14 being disposed therein. The combination 10 is sterilizable for operating room use and an outer pouch may be provided in which the combination 10 is packaged to maintain sterility thereof.

Figure 1:
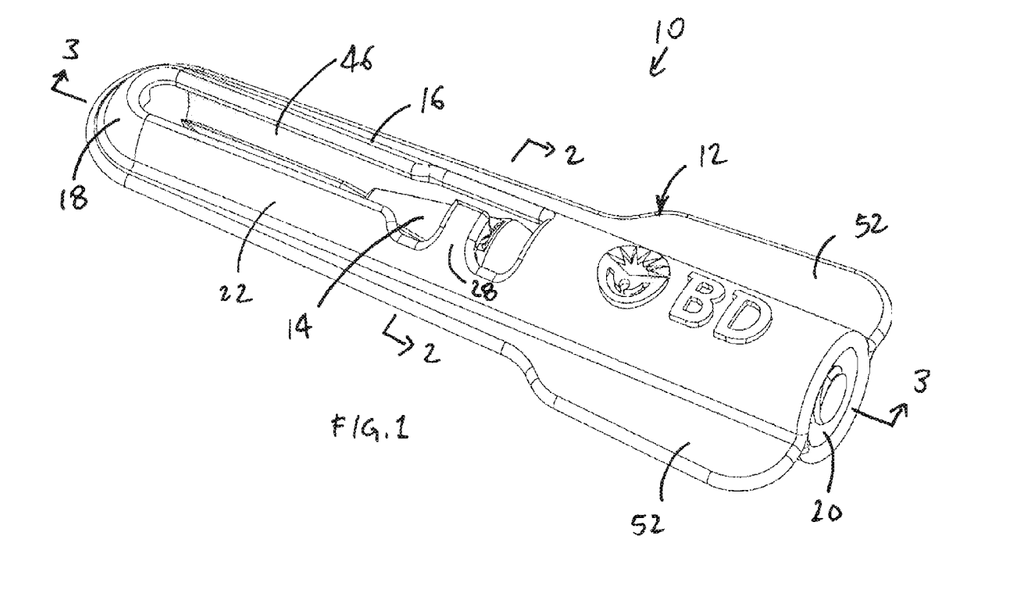
FIG. 1 is a perspective view of a package having a surgical blade tip disposed therein in accordance with the subject invention.

The package 12 includes a body 16 with a closed end 18, an open end 20 and a side wall 22 extending therebetween. The body 16 defines an interior 24 formed to accommodate the surgical blade tip 14, preferably, with no portion of the surgical blade tip 14 extending therefrom. At least two detents 26 extend inwardly from the side wall 22 into the interior 24, with, preferably, two of the detents 26 being provided which are disposed at diametrically opposite locations on the body 16. The detents 26 are formed to be deflectable. With reference to FIG. 1, the detents 26 may be formed on cantilevered arms 28 formed in the side wall 22. Outward deflection of the detents 26 may be obtained by causing the cantilevered arms 28 to deflect outwardly. Alternatively, in a preferred arrangement, as shown in FIGS. 13-16, the detents 26 may extend from the side wall 22 with the detents 26 being provided with a degree of internal resilience which permits the necessary outward deflection of the detents 26 and/or the side wall 22 adjacent to the detents 26 being thinned or formed otherwise with sufficient resilience thus permitting the necessary outward deflection.

The body 16 may be formed with various configurations. In a preferred configuration, as shown in FIGS. 13-16, the side wall 22 defines a channel 23 through which the surgical blade tip 14 may pass in being placed into the package 12 or removed therefrom. The channel 23 may extend from the closed end 18 to the open end 20. The channel 23 is formed with sufficient width to allow passage of the surgical blade tip 14 therethrough as described below. With this arrangement, the side wall 22 may be generally u-shaped with the channel 23 defining an opening into the interior 24, thereby providing the body 16 with a general tray-shape.

Figure 2:
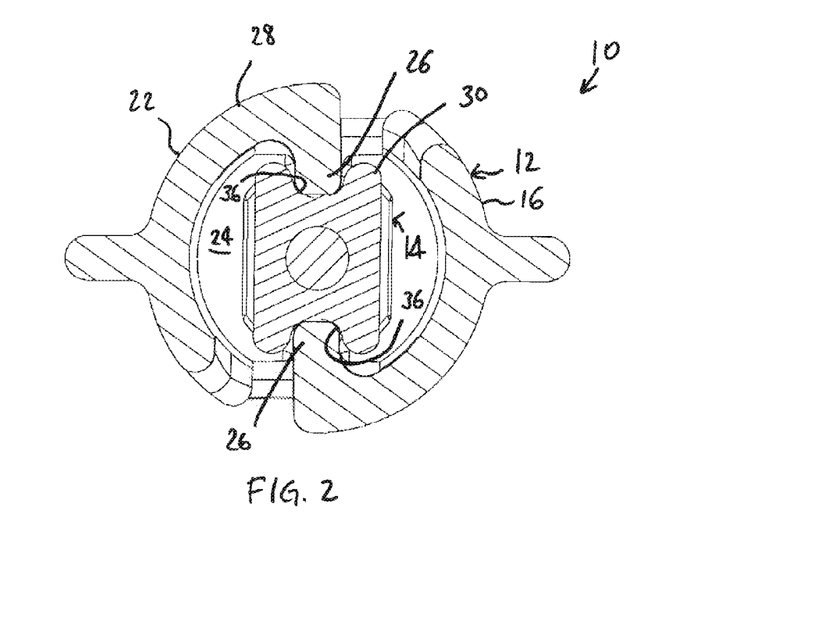
FIG. 2 is a cross-sectional view taken along line 2-2 of FIG. 1.
Figure 3:
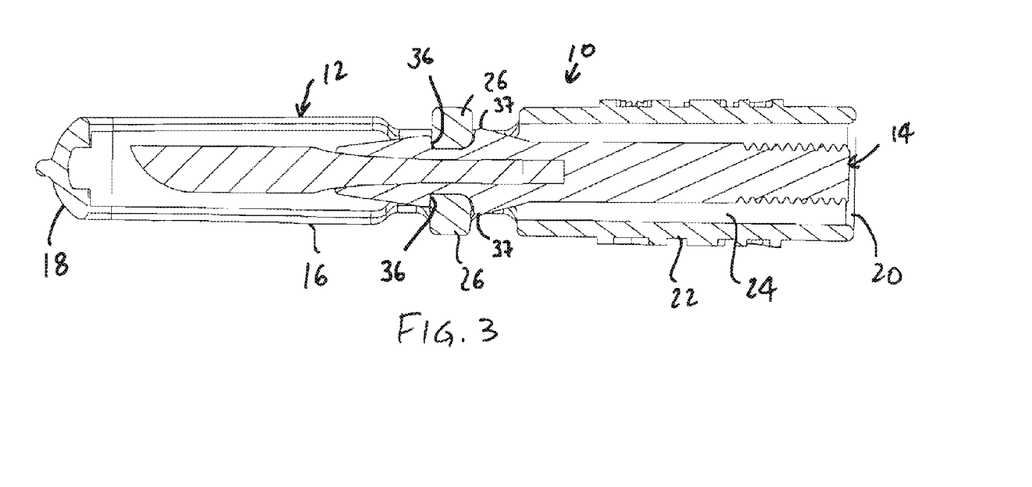
FIG. 3 is a cross-sectional view taken along line 3-3 of FIG. 1.

Alternatively, as shown in FIGS. 1-3, at least portions of the side wall 22 may circumscribe the interior 24. In this manner, the side wall 22 would at least partially circumscribe the surgical blade tip 14 with the surgical blade tip 14 being accommodated in the package 12 with the side wall 22 being configured to permit removal of the surgical blade tip 14 through the open end 20. With this arrangement, the body 16 may be tubular in shape.

The package 12 may be formed of various materials which are of sufficient robustness to provide a level of protection to the contained surgical blade tip 14 and which can withstand sterilization. Preferably, the package 12 is formed of a thermoplastic material, such as polycarbonate, delrin, ABS, polypropylene, polystyrene, polyacetal, polysulfone, PEI, and/or PEEK. In addition, the package 12 may be wholly or partially transparent or translucent to allow for inspection of the contained surgical blade tip 14 prior to use.

With reference to FIGS. 4-7, the surgical blade tip 14 includes an adaptor 30 with a blade 32 extending therefrom. The blade 32 is of any known type usable for surgery, and includes at least one sharpened edge 34. The blade 32 is affixed to the adaptor 30 in any known matter, (for example, insert-molded, press-fit, epoxy-fit, ultrasonic welding, etc.) including the blade 32 having an integral tang 33 embedded in the adaptor 30. The adaptor 30 also includes at least two recesses 36 formed therein. The recesses 36 are positioned and configured to have the detents 26 be at least partially inserted thereinto with the surgical blade 14 disposed in the package 12. Preferably, the recesses 36 are located on opposing sides of the adaptor 30. The recesses 36 may extend wholly (FIG. 14) or partially (FIG. 2) along the sides of the adaptor 30. In addition, at least one, preferably two, channels 38 are formed on the exterior of the adaptor 30 which extend between the recesses 36. The channels 38 may be formed to seatingly receive the detents 26. Preferably, the channels 38 are located on opposing sides of the adaptor 30. In a preferred arrangement, two of the recesses 36 and two of the channels 38 are located alternately about a portion of the adaptor 30 having a generally rectangular cross-section.

A raised edge 37 is provided on the adaptor 30 at least adjacent to the recesses 36. With reference to FIG. 3, the raised edge 37 engages against the detents 26 in limiting the extent the surgical blade tip 14 may be inserted into the package 12. Preferably, the raised edge 37 circumscribes the adaptor 30.

The channels 38 are preferably bound on one side with the raised edge 37 and bound on an opposing side with a front edge 39. The front edge 39 is formed with less height than the raised edge 37. The front edge 39 provides resistance against disengagement of the detents 26 with the detents 26 being seated in the channels 38, with the resistance being surmountable with a sufficient amount of pulling force being applied to withdraw the surgical blade tip 14 from the package 12, particularly through the open end 20.

The blade 32 may be formed of any material, with any preparations or coatings thereon, known in the art. The adaptor 30 may be formed of any material which is sterilizable. Preferably, the adaptor 30 is formed of a thermoplastic material, such as polycarbonate, delrin, ABS, polypropylene, polystyrene, polyacetal, polysulfone, PEI, and/or PEEK.

Figure 14:
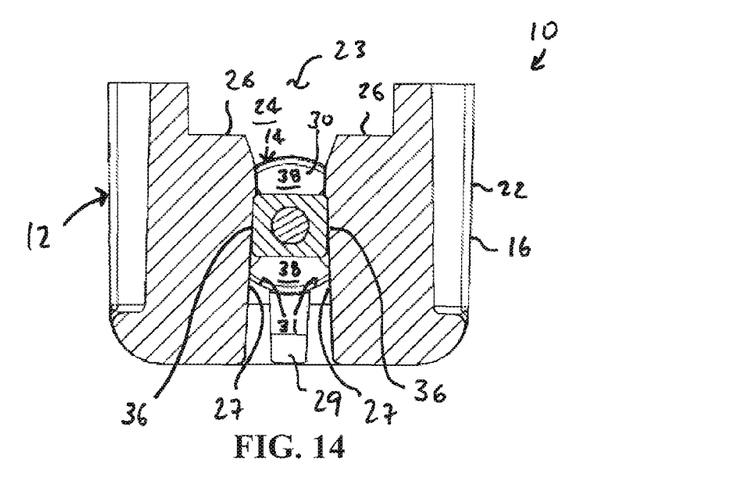
FIG. 14 is a cross-sectional view taken along line 14-14 of FIG. 13.
Figure 15:
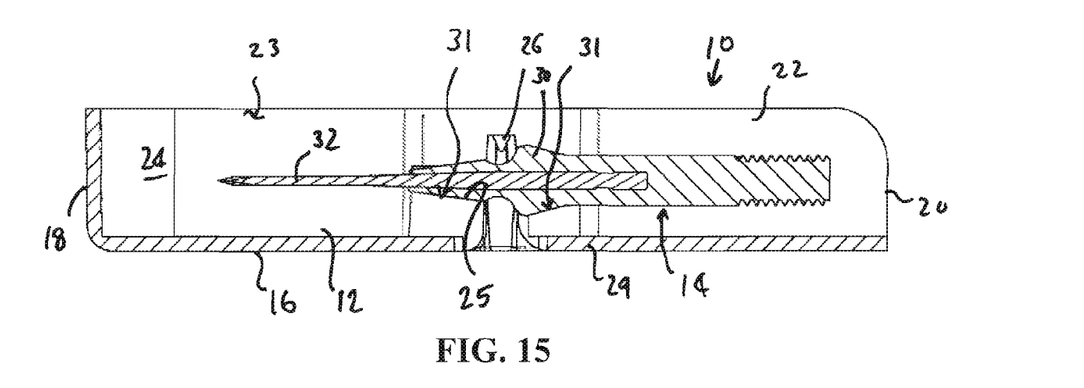
FIG. 15 is a cross-sectional view taken along line 15-15 of FIG. 13.

With reference to the Figures, the surgical blade tip 14 is initially disposed in the package 12 with the blade 32 being directed towards the closed end 18 and, preferably, with the blade 32 located closer to the closed end 18 than the adaptor 30. In addition, the detents 26 are at least partially inserted into the recesses 36. The detents 26 are configured to apply a retentive force to the adaptor 30 so as to retain the adaptor in a first position where the detents 26 are at least partially inserted into the recesses 36. The retentive force may be generated by inherent memory of the package 12, particularly at, and/or adjacent to, the detents 26. Preferably, the detents 26 are at least as long in length as the recesses 36 so as to ensure good engagement therebetween. More preferably, as shown in FIG. 14, the detents 26 are longer in length than the recesses 36 such that the detents 26 extend beyond the recesses 36. The detents 26 are also configured, as described below, to deflect with a predetermined amount of torque applied to the surgical blade tip 14 so as to permit the adaptor 30 to turn from the first position to a second position where the detents 26 are not inserted into the recesses 36.

As shown in FIG. 2, the package 12 may apply retentive force to the surgical blade tip 14 with sole contact being between the package 12 and the surgical blade tip 14 being at the interengagement of the detents 26 and the recesses 36. In this manner, the surgical blade tip 14 is held in a pinned manner by the detents 26.

More preferably, the detents 26 generate a downward force to press the adaptor 30 against portions of the package 12. In this manner, the detents 26 hold the surgical blade tip 14 in a clamping manner. In particular, as best shown in FIG. 14, the detents 26 each terminate at free end 27 which engages against the adaptor 30 with the adaptor 30 being in the first position. Preferably, the free ends 27 are angularly disposed so as to converge in extending away from a base region 29 of the side wall 22. Preferably, the free ends 27 are configured to transmit forces having force components which act inwardly against the adaptor 30, i.e., to provide a pinching effect against the adaptor 30, and also which act downwardly to urge the adaptor 30 towards the base region 29.

Figure 16:
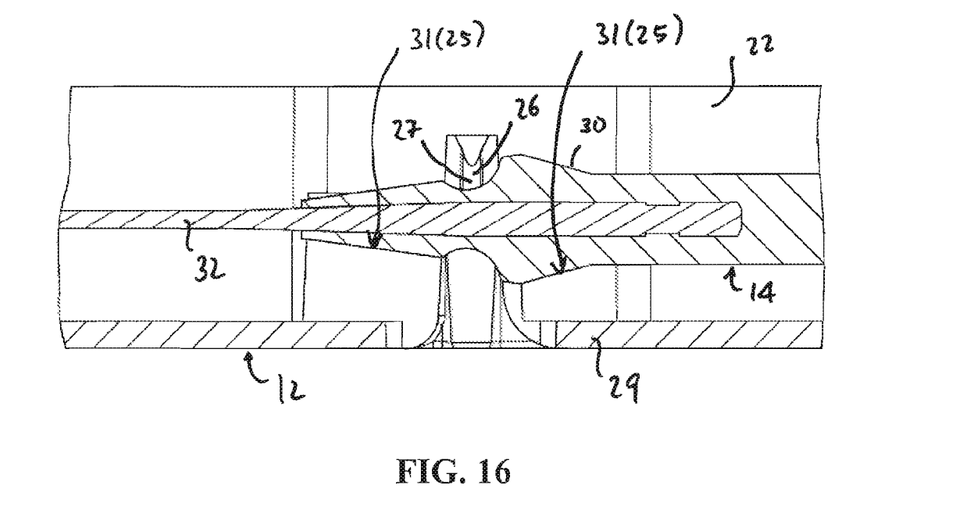
FIG. 16 is an enlarged view of a section of FIG. 15.

The adaptor 30 may be pressed against the base region 29 under force of the detents 26. It is preferred that the adaptor 30 be retained with the blade 32 being wholly contained within, and spaced from, the package 12. As shown in FIG. 16, the adaptor 30 may have an irregular cross-section which may impede or altogether prevent the blade 32 from being wholly contained within, and/or spaced from, the package 12 where downward pressing force is applied to the adaptor 30. One or more supporting surfaces 31 may be defined on the package 12 shaped to supportingly accommodate the surgical blade tip 14, preferably at the adaptor 30. It is preferred that the supporting surfaces 31 collectively define a cradle 25 on which the surgical blade tip 14 may be supported against force of the detents 26, with the adaptor 26 being in the first position. More preferably, the blade 32 is wholly contained within, and spaced from, the package 12 when supported by the cradle 25. It is further preferred that at least one supporting surface 31 be located on each side of the detents 26—at least one supporting surface 31 being located between the detents 26 and the closed end 18, and at least one supporting surface 31 being located between the detents 26 and the open end 20. In this manner, moment generated by the detents 26 in the plane shown in FIG. 16 can be counteracted. It is preferred that the cradle 25 maintain the blade 32 generally parallel to the base region 29.

Figure 4:
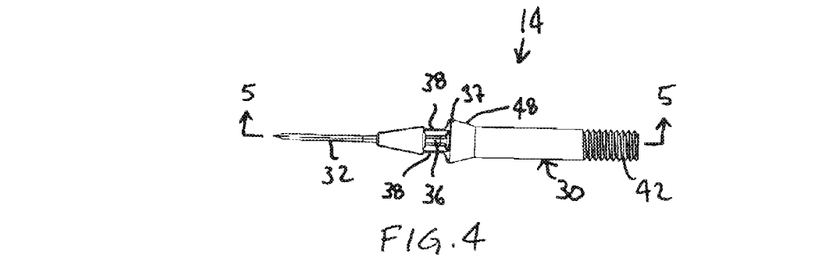
FIG. 4 is a side elevational view of a surgical blade tip useable with the subject invention.
Figure 5:
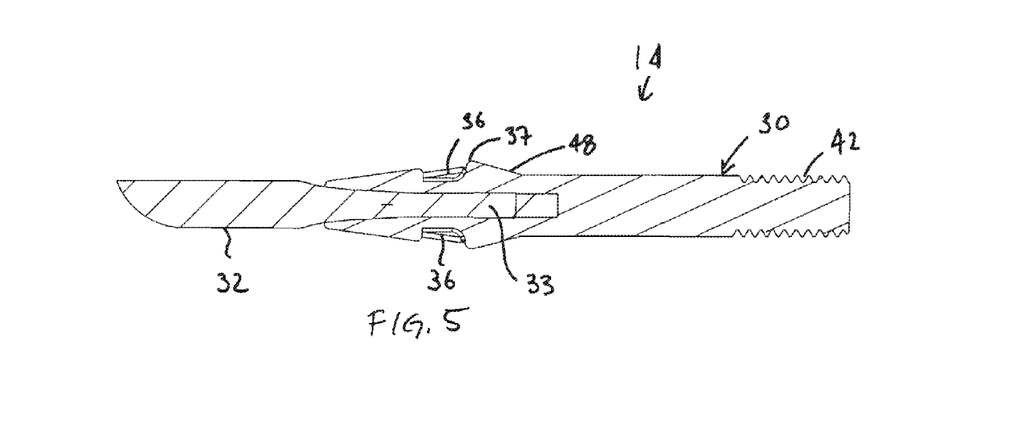
FIG. 5 is a cross-sectional view taken along line 5-5 of FIG. 4.
Figure 6:
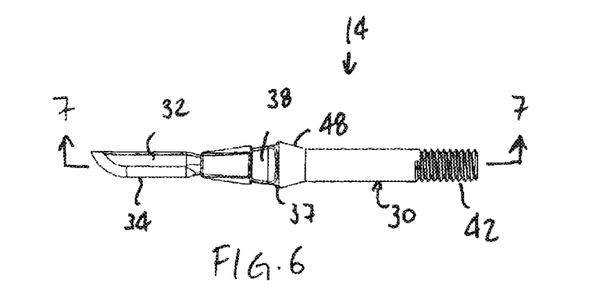
FIG. 6 is a top plan view of the surgical blade tip of FIG. 4.
Figure 7:
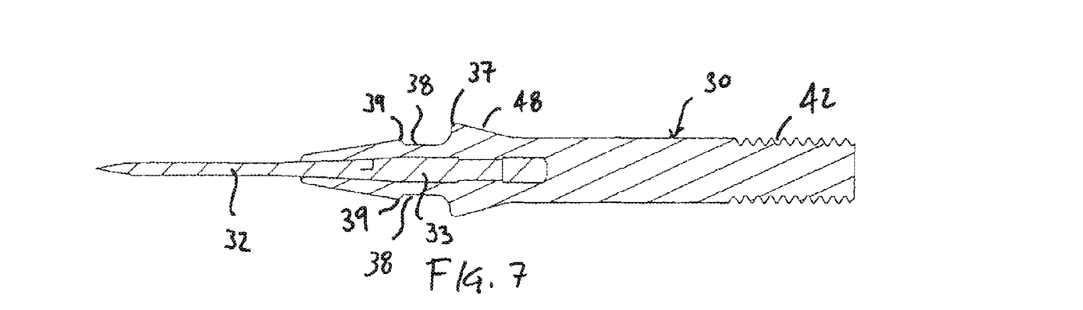
FIG. 7 is a cross-sectional view taken along line 7-7 of FIG. 6.
Figure 8:
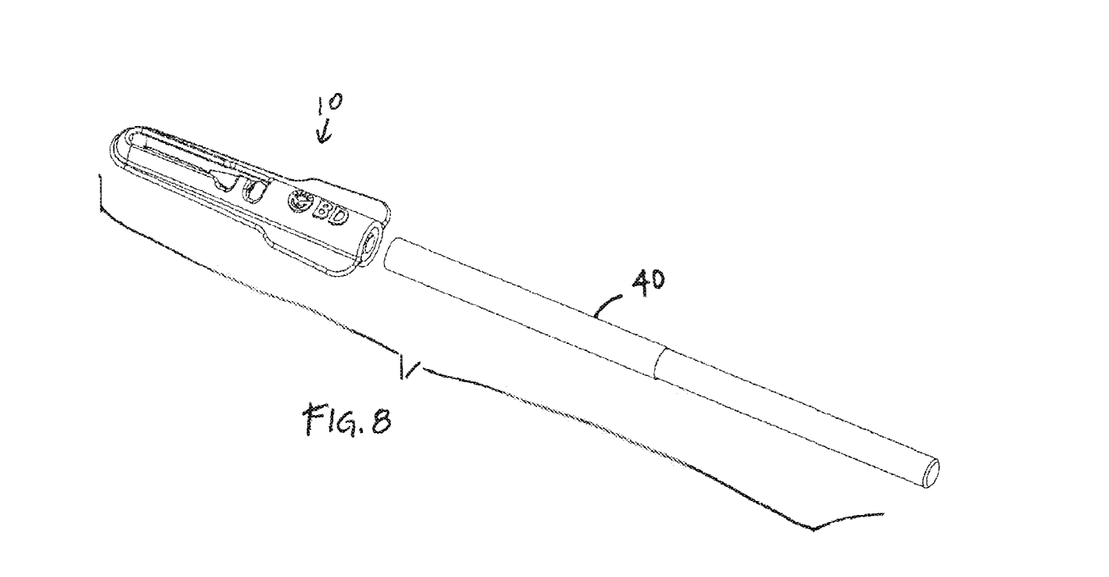
FIGS. 8-12 depict a process of preparing a surgical instrument in accordance with the subject invention.

The combination 10 may be used in the preparation of a surgical instrument. Initially, a surgical handle 40 is introduced. With reference to FIGS. 4 and 6, the adaptor 30 may be provided with features 42 for mounting onto the surgical handle 40, including being provided with threads. The surgical handle 40 is provided with cooperating features 44 (FIG. 10), such as cooperating threads.

Figure 9:
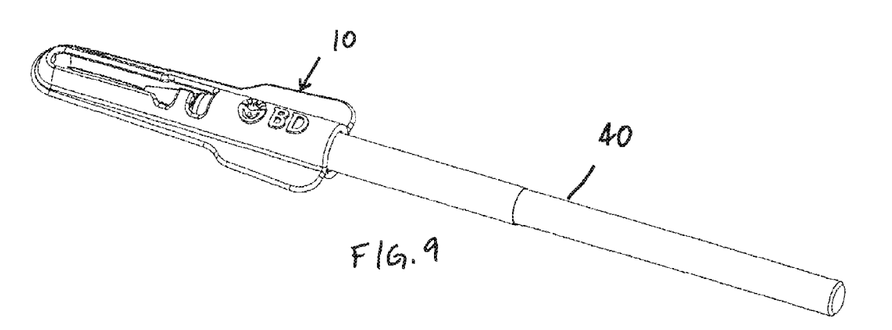
Figure 10:
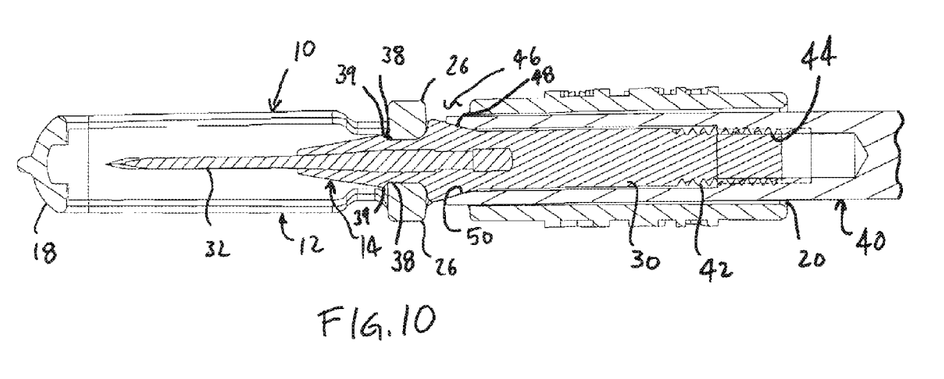

With reference to FIG. 9, the surgical handle 40 is inserted into the tubular body 16. With reference to FIG. 10, the surgical handle 40 is twisted relative to the package 12 such that threads 42 on the adaptor 30 are cooperatively engaged by threads 44 formed on the surgical handle 40. The surgical handle 40 is continued to be twisted until the threads 42 and 44 completely threadedly mate. A user may apply pressure to one or more of the detents 26, e.g., by squeezing the package 12, so as to increase the retentive force of the detents 26 acting on the surgical blade tip 14 during mounting of the surgical handle 40.

Figure 11:
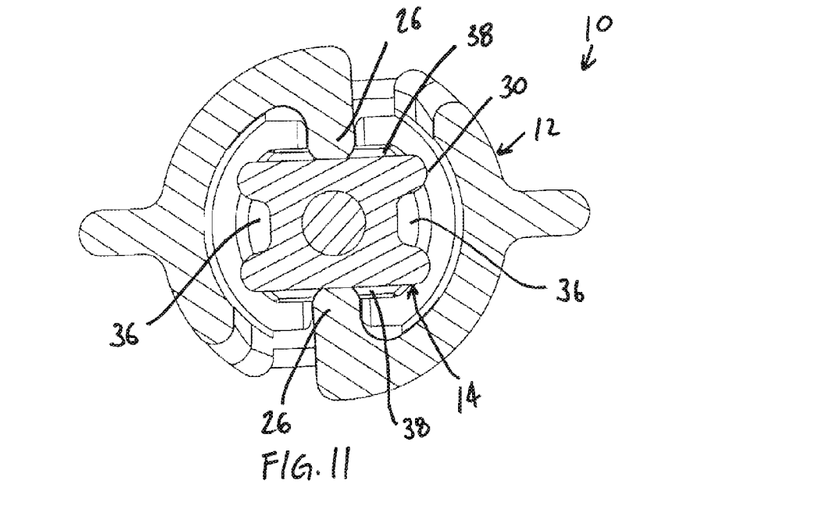
Figure 17:
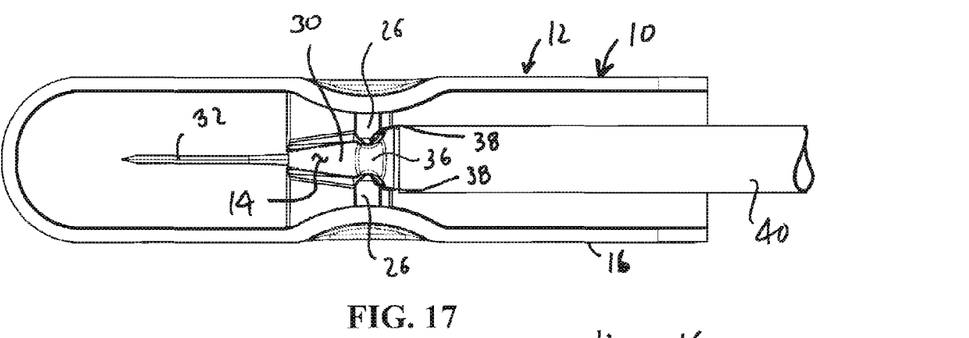
FIGS. 17-19 depict a portion of a process of preparing a surgical instrument in accordance with the subject invention.
Figure 18:
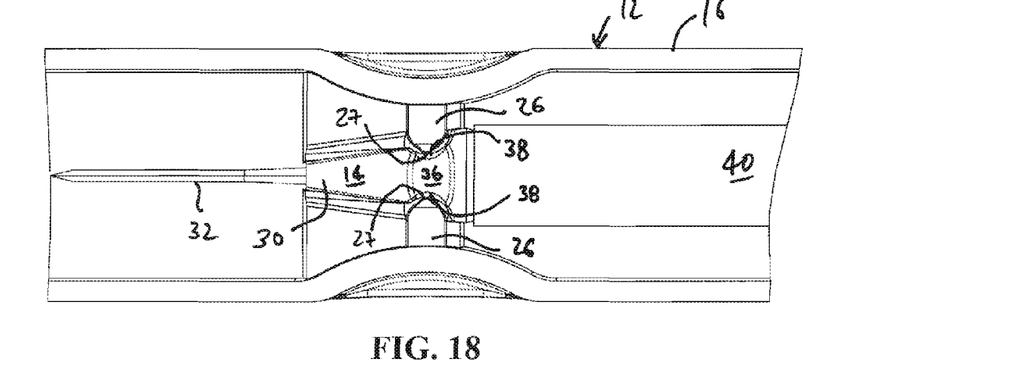

Once the surgical handle 40 is mounted, the user then applies sufficient torque (i.e., more than a predetermined amount) to disengage the detents 26 from the recesses 36 and to cause the surgical blade tip 14 to rotate relative to the tubular body 16. With sufficient torque, as shown in FIGS. 10 and 11, the surgical blade tip 14 is rotated with the detents 26 becoming disengaged from the recesses 36. Advantageously, the disengagement may provide an audible click thereby providing a user with an auditory signal that the surgical blade tip 14 has been sufficiently rotated. The detents 26, upon rotation, become aligned with the channels 38, as shown in FIGS. 10, 11 and 17, 18. In alignment, the detents 26 may be partially or wholly seated in the channels 38, although the detents 26 alternatively may be sufficiently spaced from the adaptor 30 so as to not be seated in the channels 38. Preferably, a 90 degree rotation of the surgical blade tip 14 relative to the body 16 is required to shift the surgical blade tip 14 from the first position shown in FIG. 2/FIG. 14 (with the detents 26 engaging the recesses 36) to the second position shown in FIG. 11/FIGS. 17, 18 (with the detents 26 aligned with the channels 38). FIGS. 2 and 11 show the package 12 with the body 16 being tubular; FIGS. 14, 17 and 18 show the surgical blade tip 14 disposed in the body 16 having the channel 23.

Figure 12:
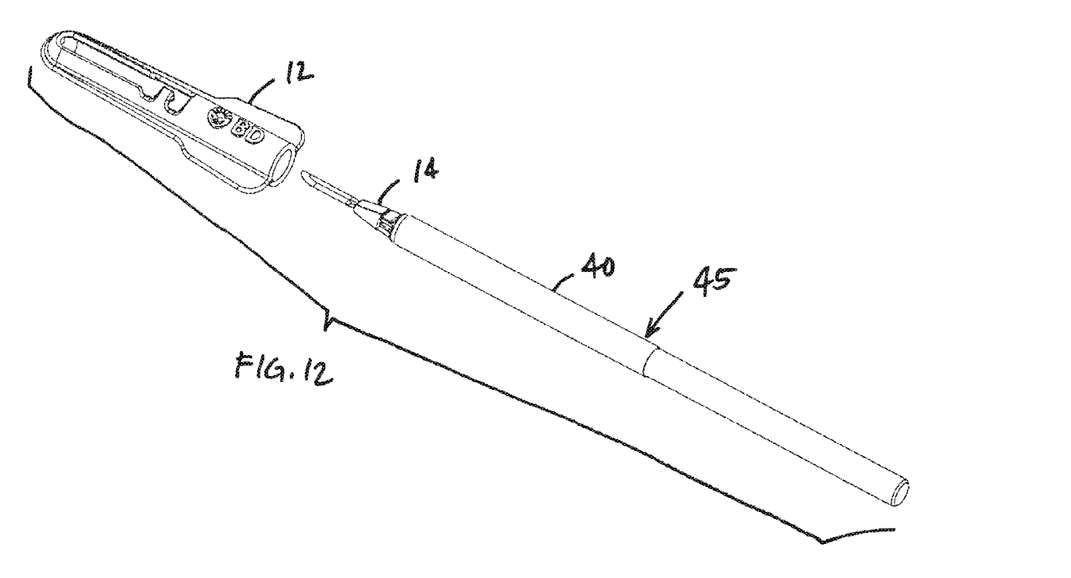
Figure 13:
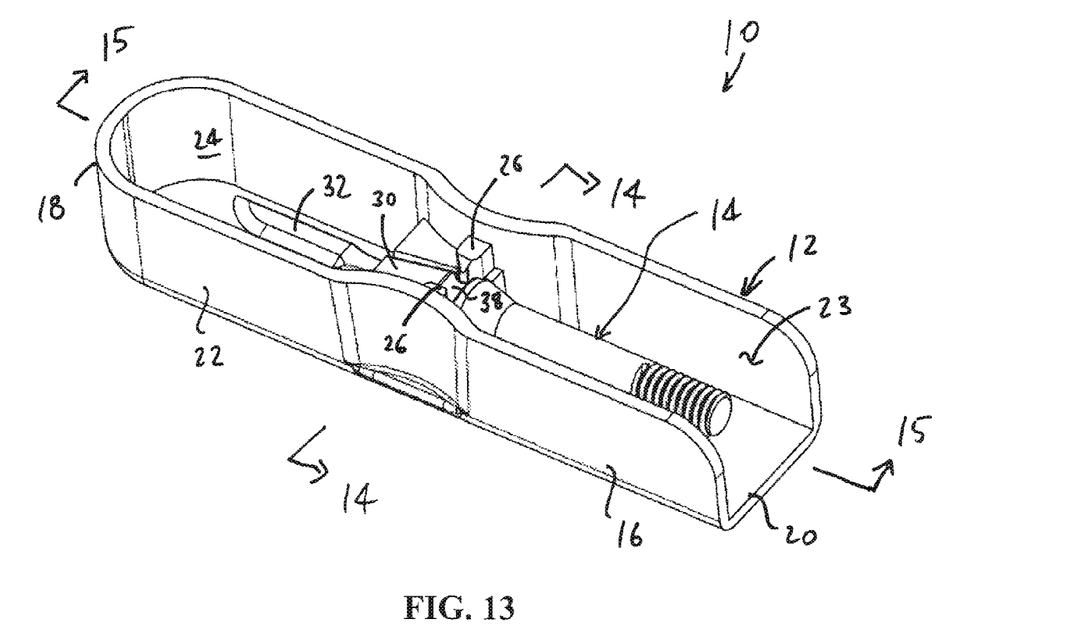
FIG. 13 is a perspective view of a package having a surgical blade tip disposed therein in accordance with the subject invention.
Figure 19:
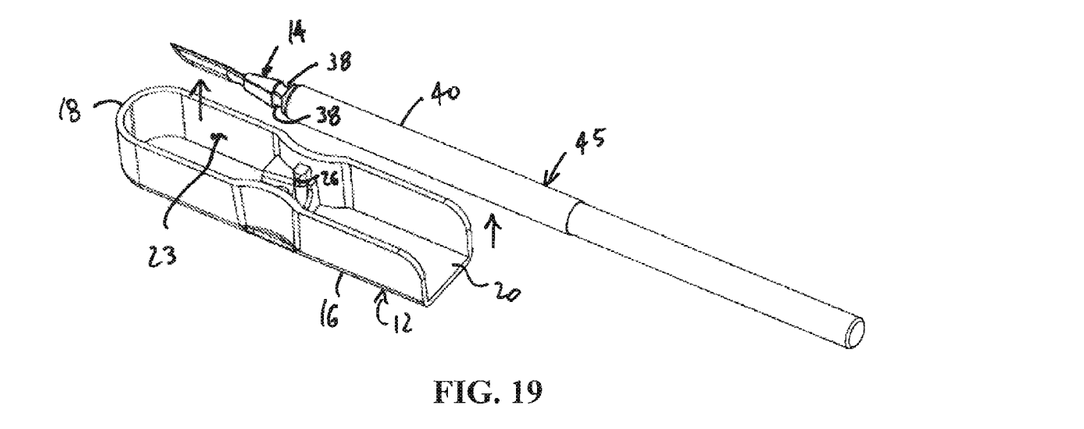

Once the surgical blade tip 14 has been rotated to have the detents 26 aligned with the channels 38, removal of the surgical blade tip 14 from the package 12 depends on the configuration of the package 12. With the configuration of the package 12 as shown in FIGS. 1-3, sufficient pulling force may be applied to the surgical handle 40 to pull the surgical handle 40 away from the package 12 such that the detents 26 deflect to surmount the front edge 39 and separate from the channels 38. With disengagement, the surgical blade tip 14 may be withdrawn from the package 12 with the surgical handle 40, as shown in FIG. 12, particularly though the open end 20. Alternatively, with the preferred configuration of the package 12 as shown in FIG. 19, the surgical blade tip 14 may be removed from the package 12 through the channel 23. In this arrangement, the surgical blade tip 14 is lifted relative to the detents 26 so as to cause separation of the channels 38 from the detents 26. The surgical blade 14 and the surgical handle 40 collectively form a surgical instrument 45 ready for use.

Preferably, with the body 16 having the channel 23, the detents 26 are sufficiently seated in the channels 38 so as to prevent forward or backward movement of the surgical blade tip 14 relative to the body 16. In particular, movement of the surgical blade tip 14 towards the closed end 18 and movement towards the open end 20 are prevented. By preventing movement towards the closed end 18, contact between the blade 32 and the closed end 18 may be avoided. Also, by preventing movement towards the open end 20, possible contact between the blade 32, particularly the sharpened edge 34, and the detents 26 may be avoided.

To facilitate use, a window 46, e.g. as shown in FIG. 1, may be formed in the side wall 22 allowing a user to confirm the type of the surgical blade tip 14 and to observe rotational displacement of the surgical blade tip 14 during use. It is also preferred, as shown in FIG. 10, that the surgical handle 40 be visible through the window 46 to indicate that it is completely threadedly mated to the surgical blade tip 14. The adaptor 30 may have a tapered section 48 for engaging with a similarly shaped front section 50 (FIG. 10) on the surgical handle 40. The interengagement of the two surfaces 48, 50 may provide a friction fit which limits reverse rotation between the surgical blade tip 14 and the surgical handle 40, thus limiting inadvertent disengagement therebetween. Further, one or more wings 52, e.g. as shown in FIG. 1, may be provided to extend outwardly from the side wall 22 to be engaged by a user during use. The wings 52 may provide surfaces for a user to better counteract the torque being applied to the surgical handle 40 during use. The wings 52 may be also used with the body 16 having the channel 23, where the wings 52 defining surfaces for better counteracting the force required to lift the surgical blade tip 14 from the package 12.

In addition, the package 12 may be utilized to dismount the surgical blade tip 14 from the surgical handle 40 to permit proper disposal of the surgical blade 14 and re-use of the surgical handle 40. The dismounting procedure is the reverse of the mounting procedure described above. In particular, to permit dismount, the surgical instrument 45, after use, is inserted into the package 12, e.g., through the channel 23 or with the surgical blade tip 14 being first inserted through the open end 18. With sufficient insertion, the detents 26 become seated in the channels 38. With rotation of the surgical instrument, the detents 26 disengage from the channels 38 and engage the recesses 36. The surgical handle 40 may then be disengaged (for example, by un-threading) from the surgical blade tip 14. Pressure may be applied to one or more of the detents 26 to ensure proper holding force for the surgical blade 14 during disengagement of the surgical handle 40.

Figure 20:
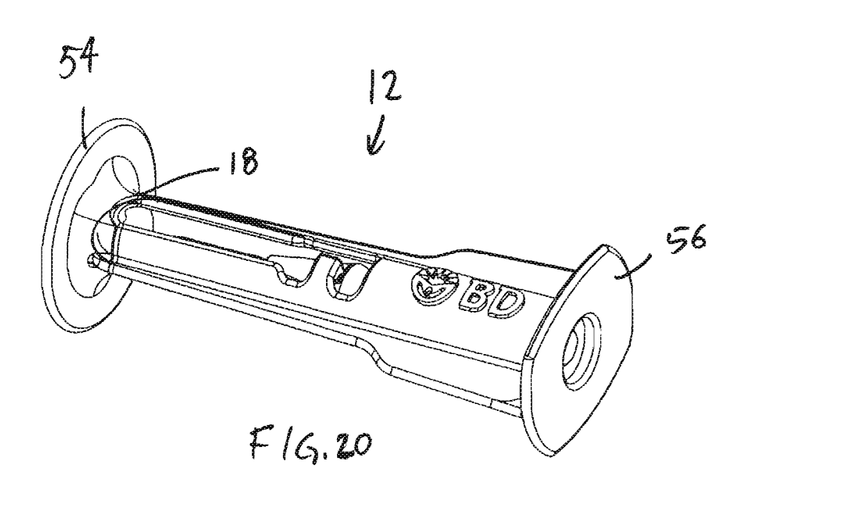
FIGS. 20-21 depict alternate package designs which are capable of freestanding.

To facilitate dismount, as shown in FIG. 20, a flattened stand 54 may be provided at the closed end 18 of the package 12 to permit the package 12 to be freestanding. This permits insertion of the surgical blade tip 14 into the package 12 after use without a user having to hold the package. The flattened stand 54 has a flat bottom configured to provide a stable resting surface which may support the package 12 in allowing the package 12 to be freestanding.

Figure 21:
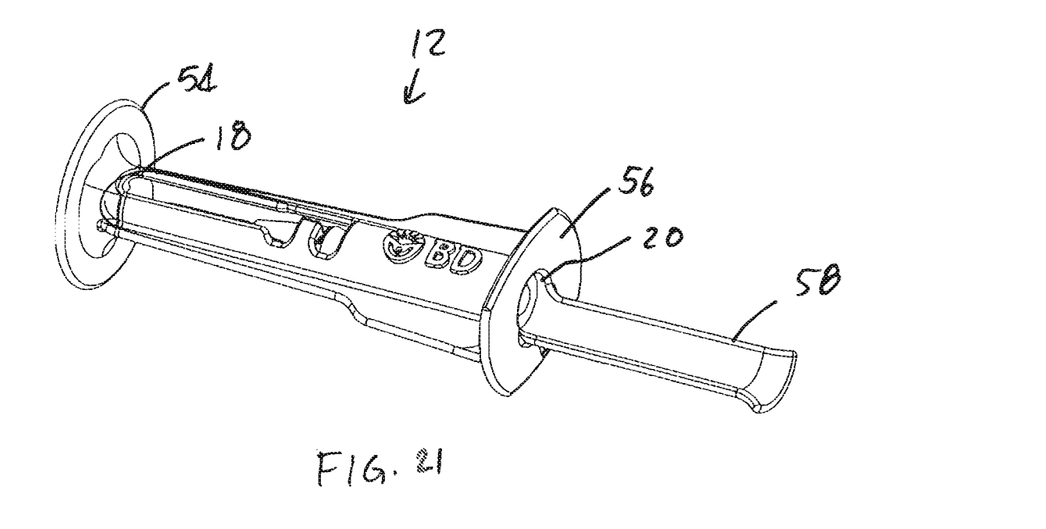
Figure 22:
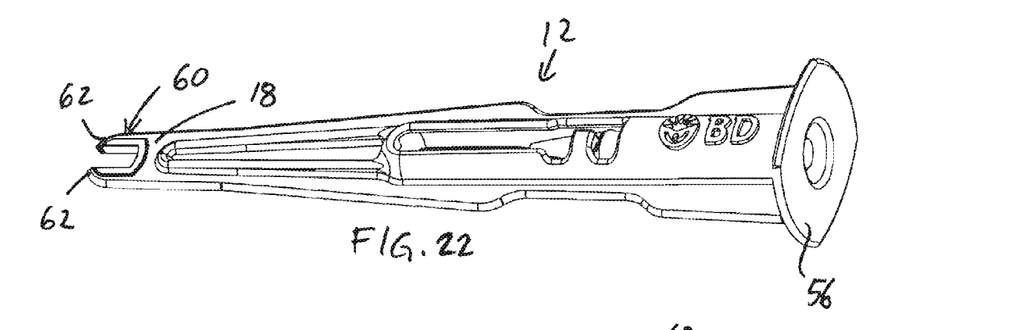
FIGS. 22-25 depict an alternate package design utilizing a wrench with FIG. 24 being a partial cross-sectional view taken along line 24-24 of FIG. 23.

A flange 56 may be formed about the open end 20 to shield a user's hand upon insertion of the surgical blade tip 14 into the package 12. The flange 56 may also protect a user's hand when the surgical blade tip 14 is removed from the package 12 as part of the surgical instrument 45. Optionally, as shown in FIG. 21, a guide 58 may be provided to extend from the open end 20 configured to guide the surgical blade tip 14 out of the package 12, thereby decreasing the possibility of the surgical blade tip 14 coming into contact with the package 12 during removal. The guide 58 is also configured to guide the surgical blade tip 14 into the open end 20 after use.

Figures 23, 24, 25:
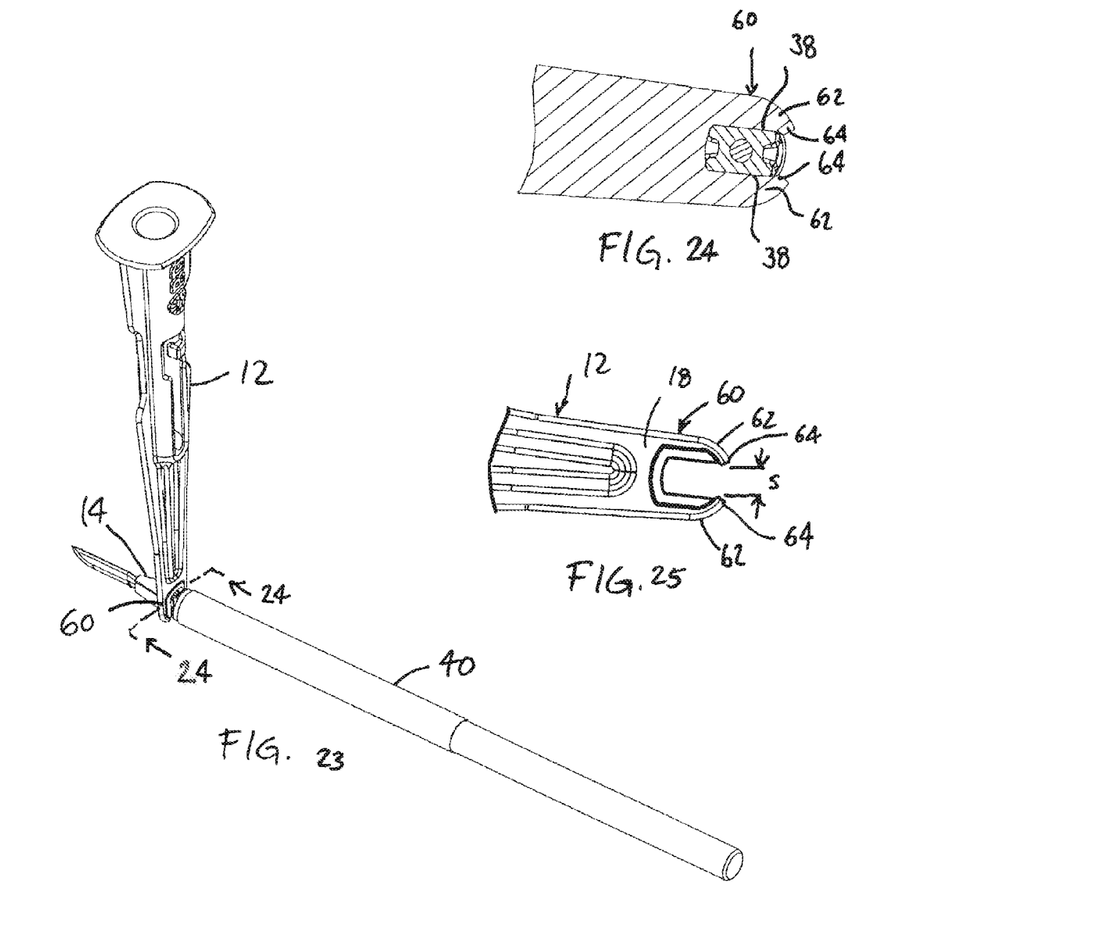

With reference to FIGS. 22-25, as an alternative, a wrench 60 may be provided on the closed end 18 formed to engage the channels 38 on the surgical blade tip 14. The wrench 60 includes tines 62 spaced apart to tightly engage the channels 38 and are preferably formed with sufficient length to extend past the channels 38. Preferably, ends 64 of the tines 62 are bent inwardly such that the spacing S between the ends 64 is less than the spacing between the channels 38. In this manner, the channels 38 may be firmly engaged by the wrench 60, including by snap engagement. The tines 62 may be configured to be fixedly attached to the channels 38 so that the package 12 is disposed with the surgical blade tip 14. As shown in FIG. 23, with torque being applied to the package 12, the wrench 60 can be used to disengage the surgical blade 14 from the surgical handle 40.

What is claimed is:

1. A combination comprising:
    a package including a body having a first closed end, a second open end, and a side wall extending therebetween, said side wall defining a base region, at least two detents extending inwardly from said side wall, said base region extending between said detents, said detents each terminating at a free end, said free ends being angularly disposed so as to converge in forming a trapezoidal shape wherein the distance between the free ends away from said base region is less than the distance between said detents adjacent to said base region; and, a surgical blade tip having an adaptor and a blade extending therefrom, said blade having at least one sharpened edge, said adaptor having at least two recesses formed therein, wherein, said surgical blade tip being disposed in said package with said blade being directed towards said first closed end, said detents, while being at least partially inserted into said recesses, are configured to apply a retentive force to said adaptor to retain said adaptor in a first position and to urge said adaptor towards said base region, wherein said detents being configured to deflect with a predetermined amount of torque being applied to said surgical blade tip so as to permit said adaptor to rotate relative to said body from said first position to a second position where said detents are not inserted into said recesses.

2. A combination as in claim 1, wherein said detents are disposed at diametrically opposite locations on said body.

3. A combination as in claim 1, wherein said detents are deflectable to disengage from said recesses.

4. A combination as in claim 1, wherein said adaptor includes at least one channel formed on the exterior thereof extending between said recesses.

5. A combination as in claim 4, wherein said channel is formed to seatingly receive at least one said detent.

6. A combination as in claim 5, wherein said detents are deflectable to disengage from said channel.

7. A combination as in claim 1, wherein said adaptor includes features for mounting onto a surgical blade handle.

8. A combination as in claim 7, wherein said features include threads.

9. A combination as in claim 1, wherein said package includes a flange disposed about said second open end.

10. A combination as in claim 1, wherein at least portions of said side wall circumscribe said surgical blade tip with said surgical blade tip being disposed in said package.

11. A combination as in claim 1, wherein said side wall defines a channel configured such that said surgical blade tip may be removed from said package through said channel.

12. A combination as in claim 11, wherein said channel extends from said first closed end to said second open end.

13. A combination as in claim 1, wherein said package includes a stand extending from said first closed end, said stand defining a flat resting surface configured to support said package in a standing position.

14. A combination as in claim 1, wherein said package includes a wrench extending from said first closed end.

15. A combination as in claim 14, wherein said wrench being formed to engage said adaptor.

16. A combination as in claim 1, wherein, said body configured such that, with said surgical blade tip disposed in said package, said surgical blade tip being wholly located between said first closed end and said second open end.

17. A combination as in claim 1, wherein said adaptor is formed of thermoplastic material.

\* \* \* \* \*